United States Patent [19]

Jacquet et al.

[11] Patent Number: 4,545,981

[45] Date of Patent: Oct. 8, 1985

[54] NAIL ENAMEL CONTAINING POLYTETRAHYDROFURAN AS A RESIN

[75] Inventors: Bernard Jacquet, Antony; Christos Papantoniou, Montmorency; Quintino Gaetani, Bondy, all of France

[73] Assignee: L'Oreal, Paris, France

[21] Appl. No.: 443,891

[22] Filed: Nov. 23, 1982

[30] Foreign Application Priority Data

Nov. 24, 1981 [FR] France .................................. 81 21954

[51] Int. Cl.$^4$ ................................................ A61K 7/04
[52] U.S. Cl. ...................................... 424/61; 523/105
[58] Field of Search ........................ 424/61; 523/105; 524/113; 568/617

[56] References Cited

U.S. PATENT DOCUMENTS 4,126,675  11/1978  Boulogne et al. ..................... 424/61
4,229,227  10/1980  Ikeda et al. ............................ 424/61

FOREIGN PATENT DOCUMENTS 53-28661  3/1978  Japan .
2110701   6/1983  United Kingdom .

OTHER PUBLICATIONS

Gaylord, *High Polymers*, vol. XIII, Interscience 1963, pp. 293-310.

*Primary Examiner*—Sidney Marantz
*Assistant Examiner*—Sharon P. Foley
*Attorney, Agent, or Firm*—Cushman, Darby and Cushman

[57] ABSTRACT

A colored or colorless nail enamel consists essentially of at least one film forming agent, a resin and a solvent system. The enamel can also contain a plasticizing agent and/or a coloring agent. The resin is polytetrahydrofuran having the formula: $HO-[CH_2-CH_2-CH_2-CH_2-O]_nH$ wherein n is such that the average molecular mass is between 300 and 3,000,000.

8 Claims, No Drawings

NAIL ENAMEL CONTAINING POLYTETRAHYDROFURAN AS A RESIN

The present invention relates to products for the nails and especially to colored or colorless nail enamels, which are long lasting, exhibit good brightness and display excellent adhesion to the keratin of the nail.

Some principal characteristics indigenous to an acceptable nail enamel are that it is essentially non-aggressive vis-a-vis the skin and nails, it is easy to apply, it is storage stable, that is to say it exhibits good homogeneity and good stability over prolonged periods of time and, finally, that it provides a film exhibiting satisfactory characteristics.

These characteristics of the film are, principally, uniform thickness, good brightness which implies a glossy surface, excellent adhesion to the nail and satisfactory flexibility so as to avoid breaking or crumbling of the enamel.

Colored or colorless nail enamels comprise, essentially, a film forming agent, a resin, a solvent system and optionally a plasticizer.

Although various substances have been proposed as film forming agents, which substances are, principally, certain copolymers, nitrocellulose, despite its disadvantages, remains an indispensable component in compositions for nail enamels.

Nitrocellulose is however never employed alone for the films obtained therefrom lack brilliance and have a tendency to break or crumble. Moreover, the adhesion of such films on the surface of the nail is not always satisfactory. Consequently nitrocellulose is generally employed together with a modifying resin.

Among these modifying resins the only ones which usually give satisfactory results are aryl sulfonamide formaldehyde resins having a low molecular weight. They are more commonly known under the name of "Santolite", the principal ones of which are known under the names of "Santolite MHP" and "Santolite MS 80%".

These "Santolite" resins while providing films of greater flexibility also increase their hardness or durability.

Nonetheless, these known modifying resins of the aryl sulfonamide formaldehyde type exhibit certain disadvantages, especially because they are only moderately stable to light.

Moreover, these known modifying resins are susceptible of releasing formaldehyde which can irritate the skin of those users whose skin may be particularly sensitive to this substance.

It has now been found that it is possible to obtain excellent nail enamels by using as a modifying resin, polytetrahydrofuran, a non-irritating substance which provides films exhibiting characteristics equal to or greater than those of films obtained until now.

The present invention thus relates to, as a new industrial product, a nail enamel consisting essentially of a film forming agent, a resin and a solvent system, optionally in the presence of a plasticizing agent and/or a coloring material, wherein the said resin is polytetrahydrofuran of the formula:

$$HO-CH_2-CH_2-CH_2-CH_2-O)_nH$$

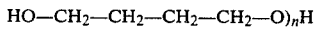

wherein n is such that the average molecular mass is between 300 and 300,000.

Preferably, the polytetrahydrofuran has an average molecular mass of 400 to 200,000 (the average mass, by weight, determined by size exclusion chromatography—tetrahydrofuran (THF) eluent column of polystyrene on "Styrogel" gel by Waters).

Polytetrahydrofuran is a known substance for which there is given, below, an example of its preparation. This compound is obtained by polymerization of tetrahydrofuran in the presence of silver hexafluoroantimonate ($AgSbF_6$) and benzyl bromide.

There can be employed, in accordance with the present invention, polytetrahydrofurans sold by BASF and especially those sold under the names of "Polytetrahydrofuran (PTHF) 650, 1000 and 2000.

These products have a softening point of about 25° to 33° C. (DIN 53180) and a density, at 25° C., of about 0.980 g/cm³ (DIN 51757).

Polytetrahydrofurans do not cause cutaneous irritation and can be considered non-toxic ($LD_{50}$ orally in a rat—5000 mg/kg).

In accordance with the present invention polytetrahydrofuran is generally present in the enamel compositions in an amount between 3 and 25 percent by weight.

The film forming agent is, preferably, nitrocellulose which can be used either alone, or in combination with a synthetic resin of the vinyl or metacrylic type, in particular, a resin such as described in French Pat. No. 80.07328. As the nitrocellulose, there can be employed those of the "RS" or "SS" type and principally nitrocellulose type ¼ second RS, nitrocellulose type ½ second RS and nitrocellulose type ¾ second RS.

Preferably, nitrocellulose of the "RS" type is employed. In accordance with the present invention, the film forming agent is generally present in the enamel composition in an amount between 5 and 27 percent and, preferably, between 6 and 20 percent relative to the total weight of the enamel.

Plasticizing agents which improve the adherence and the flexibility of the film, when they are present, are usually employed in an amount between 0.2 and 9 percent by weight and are selected from among the following substances:

tricresyl phosphate, benzyl benzoate, tributyl phosphate, butyl acetyl ricinoleate, glyceryl acetyl ricinoleate, dibutyl phthalate, butyl glycolate, dioctyl phthalate, butyl stearate, tributoxyethyl phosphate, triphenyl phosphate, triethyl citrate, tributyl citrate, tributyl acetyl citrate, 2-triethyl hexyl acetyl citrate, dibutyl tartrate, dimethoxyethyl phthalate, di-isobutyl phthalate, diamyl phthalate, camphor and their various mixtures.

By the expression "solvent system" is meant a mixture of organic solvents capable of leading to relatively short drying times for the films.

Representative solvents include, acetone, ethylacetate, butyl acetate, 2-methoxyethylacetate, methylethylketone, methylisobutyl ketone and methylacetate.

Moreover, the solvent system can also include a diluent and, preferably, an aromatic organic solvent such as toluene or xylene in an amount generally between 10 and 30 percent relative to the total weight of the enamel.

The enamel composition can also contain other volatile solvents such as ethanol, n-butanol, n-propanol, isopropanol, or their mixtures, these volatile solvents being particularly employed when the enamels contain a relatively high amount of nitrocellulose.

The nail enamel composition according to the present invention, when they are colored, contain at least one coloring agent of an inorganic or organic nature. Representative organic coloring agents include D and C Red No. 10, 11, 12 and 13, D and C Red No. 7, D and C Red No. 5 and 6, D and C Red No. 34, such lakes as D and C Yellow No. 5 lake and D and C Red No. 2 lake. Representative inorganic coloring agents include titanium dioxide, bismuth oxide, brown iron oxide, red iron oxide as well as guanine.

These coloring agents are preferably present in the enamel composition in an amount between 0.1 and 8 percent by weight relative to the total weight of the composition.

The enamel composition according to the present invention can also contain other components such as, for example, anti-sedimentation products or agents and, principally, montmorillonite type clays such as "Bentone 27" or "Bentone 38" together with a swelling agent such as orthophosphoric acid.

The following non-limiting examples are given to illustrate the present invention, the examples including not only a representative method of preparing polytetrahydrofuran but also several examples of colored or colorless nail enamel compositions.

PREPARATION OF HIGH MOLECULAR WEIGHT POLYTETRAHYDROFURAN

The polymerization reaction is carried out in a 2.5 liter reactor, fitted with means for circulating water at 20° C., a vacuum inlet, a nitrogen inlet, a thermometer, a small tube for receiving a breakable ampoule and a teflon tube connected to the receptor flask of a distillation apparatus.

A small "SVL 15" tube, fitted with a septum, permits the introduction of a reactant by means of a hypodermic syringe.

Agitation is effected by means of a vibrator. After inserting the breakable ampoule containing 3.08 g of silver hexafluoroantimonate ($9 \times 10^{-3}$ mole), the apparatus is carefully purged and maintained under pure nitrogen. There are then introduced by means of the Teflon tube, 2 liters of tetrahydrofuran purified by distillation, once over calcium hydride and a second time over sodium-naphthalene.

The breakable ampoule is then broken in the reactor and the silver salt is dissolved in a few minutes under agitation.

There are then introduced 1.54 g ($9 \times 10^{-3}$ mole) of distilled benzyl bromide, by means of the precision syringe. A rapid increase in opalescence is observed, as well as a yellowing of the reaction medium.

After about 20 minutes an appreciable increase in the viscosity is noted and the temperature is maintained at 20° C.

After a 50 minute reaction period, the polymerization is terminated by the addition of 10 ml of triethylamine in solution in methanol. The polymer is precipitated a first time in 15 liters of permuted water, then dried under a vacuum, yielding 309 grams of dry polymer.

The resulting dry polymer is then taken up in a mixture of 3 liters of methylene chloride and 3 liters of heptane. After dissolution, the solution (2610 g) is centrifuged for 1 hour at 3000 rpm. The clear supernatant is then concentrated to dryness. The polymer is dissolved again in 2 liters of tepid ethanol (40° C.) and then precipitated simply by cooling in an ice bath.

After decanting the supernatant, the polymer is finally dried under a vacuum at 20° C.

The molecular mass of the polymer thus obtained is 110,000 (average mass by weight determined by size exclusion chromatography —THF eluent—polystyrene column, "Styragel" by Waters).

EXAMPLES OF NAIL ENAMELS

Example 1

In accordance with the invention a colorless nail enamel is prepared by admixing the following components:

Polytetrahydrofuran (PTHF 650): 8 g
Nitrocellulose, ½ second: 12 g
Dibutyl phthalate: 4 g
Camphor: 2 g
Solvent mixture consisting of butyl acetate and ethyl acetate in a 2/1 ratio, sufficient amount for: 100 g

Example 2

In accordance with the present invention a colorless nail enamel is prepared by admixing the following components:

Polytetrahydrofuran (PTHF 650): 6 g
Nitrocellulose, ½ second: 12 g
Dibutylphthalate: 4 g
Camphor: 2 g
Solvent mixture consisting of butylacetate and ethylacetate in a 2/1 ratio, sufficient amount for: 100 g In this example the PTHF 650 can be replaced by the same amount of PTHF 1000 or PTHF 2000.

Example 3

In accordance with the present invention a colored nail enamel is prepared by admixing the following components:

Polytetrahydrofuran (molecular mass: 110,000): 8 g
Nitrocellulose ½ second: 12 g
Titanium dioxide: 0.3 g
Bentone 27: 1.2 g
Ferric blue (Prussian): 0.1 g
D and C Red 7—calcium lake: 0.3 g
D and C Yellow 5—aluminum lake: 0.7 g
Ethylacetate: 15 g
Toluene: 30 g
Butylacetate, sufficient amount for: 100 g

Example 4

In accordance with the invention a golden nail enamel is prepared by admixing the following components:

Polytetrahydrofuran (PTHF 1000): 4 g
Nitrocellulose, ½ second: 8 g
Polymer prepared in accordance with Example 3 of French Pat. No. 80.07328: 4 g
Titanium dioxide: 0.3 g
Bentone 27: 1.2 g
Ferric blue (Prussian): 0.1 g
D and C Red 7—calcium lake: 0.3 g
D and C Yellow 7—aluminum lake: 0.7 g
Ethylacetate: 15 g
Toluene: 30 g
Butylacetate, sufficient amount for: 100 g

Example 5

In accordance with the invention a colorless nail enamel is prepared by admixing the following components:

Polytetrahydrofuran (PTHF 2000): 4 g

Nitrocellulose, ½ second: 10 g

Polymer prepared according to Example 4 of French Pat. No. 80.07328: 3 g

Butyl phthalate: 4 g

Camphor: 2 g

Solvent mixture consisting of butyl acetate and ethyl acetate in a 2/1 ratio, sufficient amount for: 100 g

What is claimed is:

1. In a nail enamel composition comprising nitrocellulose as a film forming agent, a resin for modifying said film forming agent and a solvent, the improvement comprising said resin for modifying said film forming agent consisting essentially of polytetrahydrofuran having an average molecular mass between 300 and 300,000 as determined by size exclusion chromatography.

2. The nail enamel of claim 1 wherein the polytetrahydrofuran has an average molecular mass between 400 and 200,000.

3. The nail enamel of claim 1 wherein the polytetrahydrofuran is present in an amount between 3 and 25 percent by weight.

4. The nail enamel of claim 1 wherein the film forming agent is present in an amount between 5 and 27 percent by weight based on the total weight of the enamel.

5. The nail enamel of claim 1 which also includes a plasticizing agent present in an amount between 0.2 and 9 percent by weight based on the total weight of the enamel.

6. The nail enamel of claim 1 wherein the solvent includes a diluent selected from toluene or xylene in an amount between 10 and 30 percent by weight based on the total weight of the enamel.

7. The nail enamel of claim 1 which also includes an inorganic or organic coloring agent in an amount between 0.1 and 8 percent by weight based on the total weight of the enamel.

8. The nail enamel of claim 1 which also includes a montmorillonite type clay in the presence of orthophosphoric acid as a swelling agent.

* * * * *